United States Patent
Son et al.

(10) Patent No.: US 10,732,160 B2
(45) Date of Patent: Aug. 4, 2020

(54) PORTABLE NANOAPTAMER ANALYZER FOR DETECTION OF BISPHENOL A

(71) Applicants: Ewha University—Industry Collaboration Foundation, Seoul (KR); Korea University Research and Business Foundation, Seoul (KR)

(72) Inventors: Ah Jeong Son, Seoul (KR); Beelee Chua, Seoul (KR); Hyun Jeong Lim, Seoul (KR)

(73) Assignees: Ewha Univeristy—Industry Collaboration Foundation, Seoul (KR); Korea University Research and Business Foundation, Seoul (KR)

( * ) Notice: Subject to any disclaimer, the term of this patent is extended or adjusted under 35 U.S.C. 154(b) by 0 days.

(21) Appl. No.: 15/900,224

(22) Filed: Feb. 20, 2018

(65) Prior Publication Data

US 2018/0321204 A1 Nov. 8, 2018

(30) Foreign Application Priority Data

Feb. 21, 2017 (KR) ........................ 10-2017-0023071
Sep. 5, 2017 (KR) ........................ 10-2017-0113510

(51) Int. Cl.

| | | |
|---|---|---|
| *C12N 15/115* | (2010.01) | |
| *G01N 31/22* | (2006.01) | |
| *G01N 21/64* | (2006.01) | |
| *G01N 35/00* | (2006.01) | |
| *G01N 35/10* | (2006.01) | |
| G01N 21/31 | (2006.01) | |
| G01N 21/39 | (2006.01) | |

(52) U.S. Cl.
CPC ........... *G01N 31/22* (2013.01); *G01N 21/643* (2013.01); *G01N 35/0098* (2013.01); *G01N 35/10* (2013.01); *C12N 15/115* (2013.01); *C12N 2310/16* (2013.01); *C12N 2310/3517* (2013.01); *C12N 2320/10* (2013.01); *G01N 2021/3181* (2013.01); *G01N 2021/399* (2013.01); *G01N 2035/00346* (2013.01); *G01N 2035/00524* (2013.01); *G01N 2035/00564* (2013.01)

(58) Field of Classification Search
None
See application file for complete search history.

(56) References Cited

FOREIGN PATENT DOCUMENTS

| KR | 10-2010-0093205 A | 8/2010 |
|---|---|---|
| KR | 2010-0093502 A | 8/2010 |
| KR | 2016-0131133 A | 11/2016 |
| KR | 10-1816990 B1 | 1/2018 |

OTHER PUBLICATIONS

Ding, et al. (2015) "DNA Nanostructure-Based Magnetic Beads for Potentionnetric Aptasensing." Analytical Chemistry, vol. 87 :6465-9. (Year: 2015).*
Hyun Jeong Lim, et al., "Detection of bisphenol A using palm-size NanoAptamer analyzer", Biosensors and Bioelectronics 94 (Feb. 21, 2017) pp. 10-18.
K.V. Ragavan et al. "Functionalized aptamers as nano-bioprobes for ultrasensitive detection of bisphenol-A" Chem. Commun., 2013, 49, 5960.

* cited by examiner

*Primary Examiner* — Jennifer Pitrak McDonald
(74) *Attorney, Agent, or Firm* — John P. White; Cooper & Dunham LLP

(57) ABSTRACT

The present invention relates to a portable analyzer for detecting bisphenol A, which comprises an aptamer specifically binding to bisphenol A, and a method for detecting bisphenol A using the same. The analyzer of the present invention can analyze a small amount of a sample collected from a contaminated environment in a field at a level similar to a laboratory environment, thereby having an effect of enabling a more immediate and accurate detection and quantification of bisphenol A.

12 Claims, 11 Drawing Sheets
Specification includes a Sequence Listing.

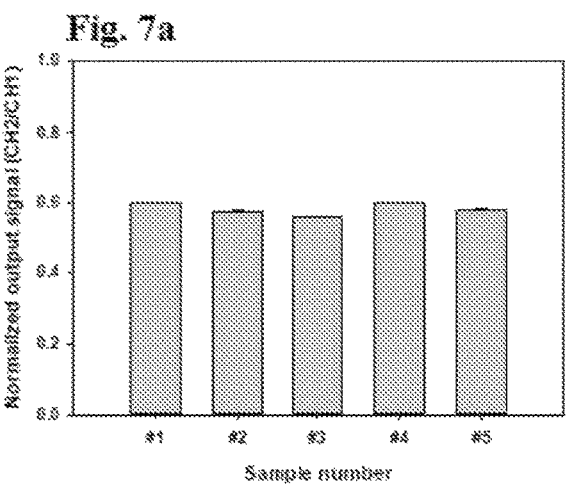
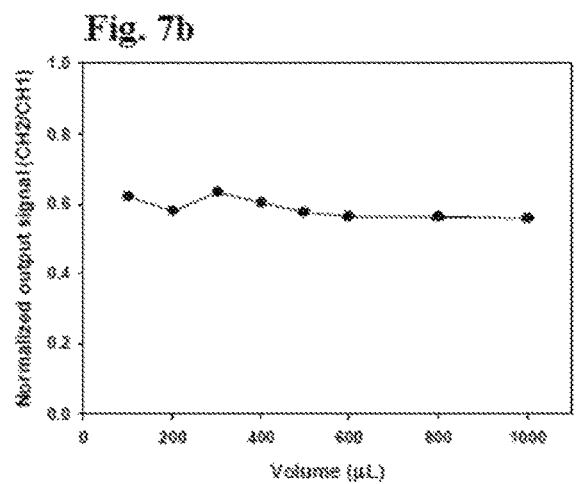
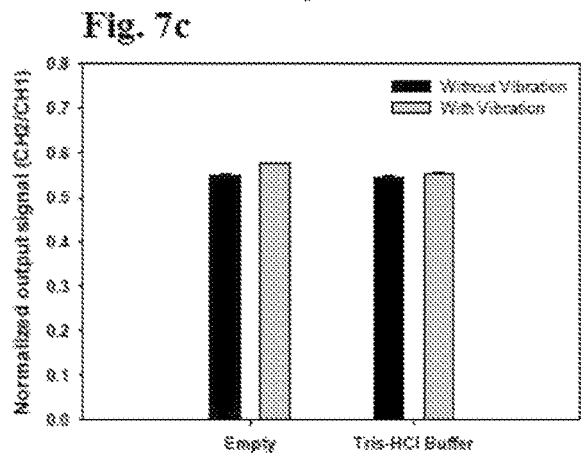
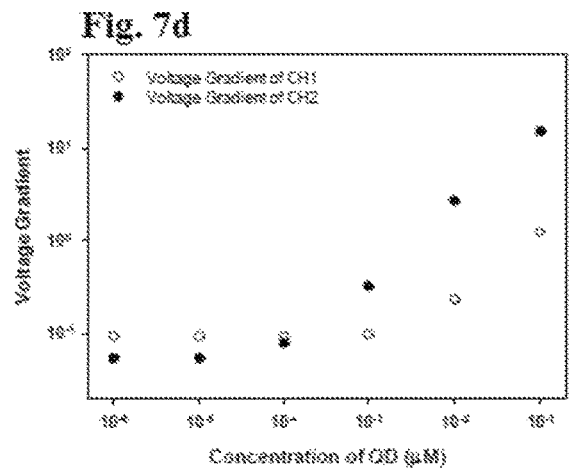
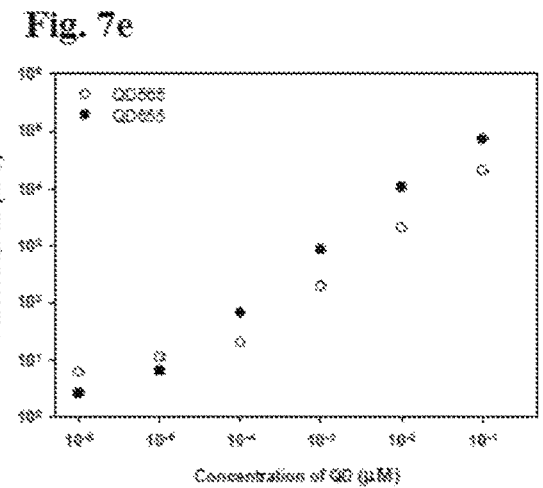

without vibration    with vibration

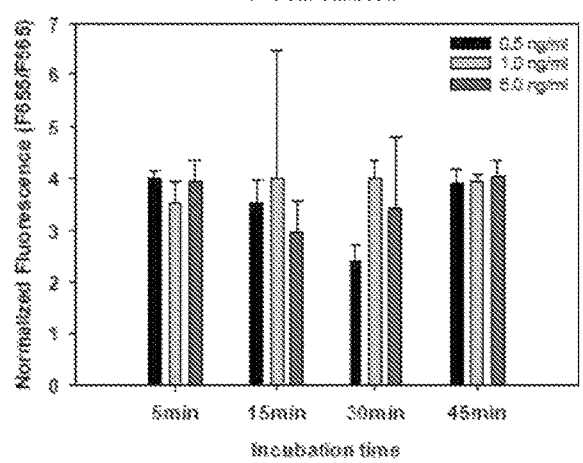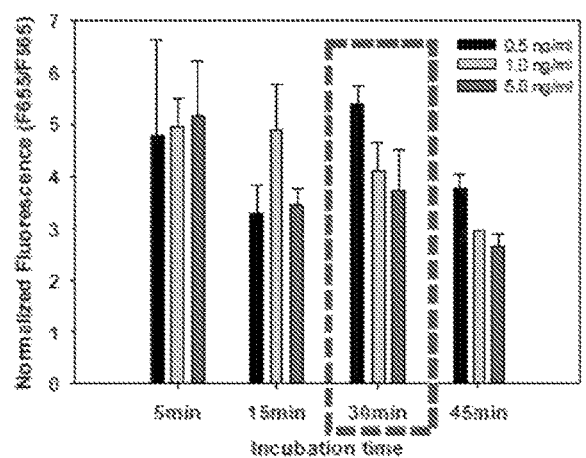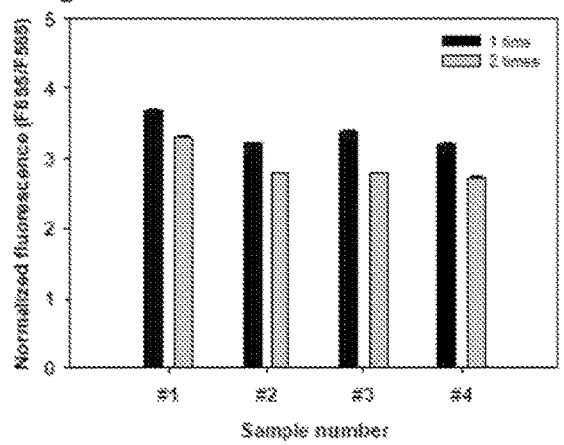

SEQUENCE LISTING

```
<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: aptamer for BPA

<400> SEQUENCE: 1
cccccctttt ggatagcggg ttcc                                          24
```

```
<210> SEQ ID NO 2
<211> LENGTH: 30
<212> TYPE: DNA
<213> ORGANISM: Artificial Sequence
<220> FEATURE:
<223> OTHER INFORMATION: probe

<400> SEQUENCE: 2
cccccctttt tatcccacct gaccacccac                                        30
```

PORTABLE NANOAPTAMER ANALYZER FOR DETECTION OF BISPHENOL A

CROSS-REFERENCE TO RELATED APPLICATIONS

This application claims priority of Korean Patent Applications Nos. KR 10-2017-0023071, filed Feb. 21, 2017, and KR 10-2017-0113510, filed Sep. 5, 2017 the contents of each of which are hereby incorporated by reference into the application.

REFERENCE TO A SEQUENCE LISTING

The application incorporates by reference nucleotide and/or amino acid sequences which are present in the file named "180220_90362_Sequence_Listing_CAE.txt", which is 767 bytes in size, and which was created Feb. 20, 2018 in the IBM-PC machine format, having an operating system compatibility with MS-Windows, which is contained in the text file filed Feb. 20, 2018 as part of this application.

TECHNICAL FIELD

The present invention relates to a portable analyzer for detecting bisphenol A, which comprises an aptamer specifically binding to bisphenol A. Additionally, the present invention relates to a method for detecting bisphenol A using the analyzer above.

BACKGROUND ART

Bisphenol A (BPA) was first synthesized and reported between the 1890s and early 1900s, and has been used in various fields, such as in the inner linings of canned foods, thermal paper for receipts, and plastic housings for electronics, toys, and baby bottles. However, it has been discovered that since bisphenol A is an endocrine-disrupting compound, and since it mimics estrogenic hormones by binding to estrogen receptors in endocrine systems, bisphenol A may cause serious health problems. Diseases caused by bisphenol A representatively include reproductive and developmental disorders in infants and children, neurological diseases, cancers, obesity, diabetes, cardiovascular diseases, etc.

The use of bisphenol A has been prohibited due to its environmental and public health implications, but contamination of rivers and reservoirs has continued due to effluents from wastewater treatment plants or leachates from landfills.

In particular, bisphenol A is known to cause such health problems at very low concentrations ($10^{-10}$ mol/L to $10^{-8}$ mol/L (0.02 ng/mL to 2.28 ng/mL, or ppb)), and thus the risk thereof is much greater. In this regard, the perpetual contamination of water supplies by bisphenol A has become one of the primary concerns of environmental and public health agencies.

Accordingly, the importance of laboratory-based and portable quantitative analysis for detecting bisphenol A contamination has gradually increased. Conventional laboratory-based analyses include gas chromatography with mass spectrometry (GC-MS), high-pressure liquid chromatography (HPLC), and a DNA Y junction sensing method, but these have problems in that they are highly dependent on the stability of antibodies and susceptible to nonspecific binding with analog compounds as well as interference from ionic species. Meanwhile, although conventional electrochemical detection has portability via screen-printed electrodes, it is problematic in that it is vulnerable to interfering species.

As one method for detection of bisphenol A, an aptamer for detecting bisphenol A has been developed. For example, Korean Patent Publication No. 2010-0093205 discloses a kit for detecting bisphenol A, which comprises two aptamers specifically binding to bisphenol A. However, bisphenol A, in which two phenol compounds are structurally linked, has a relatively simple structure, whereas the aptamer for detecting bisphenol A has a complicated two-dimensional structure having a large number of stem-loop structures; therefore, the problem has been raised that the bisphenol A detection sensitivity by the aptamer is low. However, solutions to such problem have not yet been provided.

Accordingly, the present inventors have developed a novel aptamer consisting of 14 nucleotides capable of detecting bisphenol A with higher detection sensitivity, through previous studies.

Under these circumstances, the present inventors have endeavored to develop a small nano-aptamer analyzer which is capable of detecting bisphenol A at a concentration level (<1 ng/mL or ppb) at which bisphenol A is present in the environment using the aptamer and which is capable of detecting bisphenol A in the field due to its portability. As a result, they have developed a portable analyzer capable of detecting bisphenol A using the aptamer, and have confirmed that the analyzer can detect bisphenol A at a level equivalent to the results of laboratory-based quantitative analysis of bisphenol A, thereby completing the present invention.

DISCLOSURE

Technical Problem

An object of the present invention is to provide a portable analyzer for detecting bisphenol A, comprising:
  (a) a reaction unit, which comprises:
    (i) a first complex comprising a magnetic bead, a first labeling material, a second labeling material, and an aptamer specifically binding to bisphenol A;
    (ii) a reaction vessel having an inlet, wherein the first complex reacts with bisphenol A to faun a second complex comprising the magnetic bead, the first labeling material, and the aptamer and wherein a reaction by which a second labeling material is separated from the first complex is performed; and
    (iii) a means for collecting the second complex in the reaction vessel; and
  (b) a detection unit having a means for detecting signals generated from the first and second labeling materials.

Another object of the present invention is to provide a method for detecting bisphenol A using a portable analyzer for detecting bisphenol A, comprising injecting a collected sample into an inlet.

Technical Solution

In one aspect of the present invention to achieve the above objects, the present invention provides a portable analyzer for detecting bisphenol A, comprising:
  (c) a reaction unit, which comprises:
    (i) a first complex comprising a magnetic bead, a first labeling material, a second labeling material, and an aptamer specifically binding to bisphenol A;
    (ii) a reaction vessel having an inlet, wherein the first complex reacts with bisphenol A to form a second complex comprising the magnetic bead, the first labeling material, and the aptamer and wherein a reaction by which a second labeling material is separated from the first complex is performed; and (iii) a means for collecting the second complex in the reaction vessel; and (d) a detection unit having a means for detecting signals generated from the first and second labeling materials.

The present inventors have conducted various studies to develop a technique capable of detecting bisphenol A with higher detection sensitivity, and as a result, they have developed an aptamer consisting of the nucleotide sequence of SEQ ID NO: 1, which is capable of detecting bisphenol A (Korean Patent No. 1816990).

The developed aptamer can specifically bind to bisphenol A, and has a small size compared to that of a conventional aptamer, and further, has a simple two-dimensional structure. In addition, the developed aptamer shows higher detection sensitivity to bisphenol A compared to that of a conventional aptamer.

Accordingly, the present inventors have collected samples in an environment susceptible to contamination of bisphenol A using the developed aptamer, thereby developing a portable analyzer capable of directly detecting bisphenol A in the field.

The portable analyzer according to the present invention consists of complexes comprising a magnetic bead, a labeling material, and the aptamer, and measures signals varying depending on the binding of bisphenol A, thereby detecting bisphenol A at a high sensitivity in an environment outside a laboratory.

Specifically, $QD_{565}$ encapsulated magnetic beads (MB) are bound with a bisphenol A-specific aptamer by a covalent bond, and are hybridized with a signaling DNA-$QD_{655}$ conjugate (FIG. 1a). Upon exposure to bisphenol A (incubation), the signaling DNA-$QD_{655}$ conjugate is released from the aptamer and removed (rinsed). In this way, the fluorescence signal decreased from $QD_{655}$ (fluorescence measurement) indicates BPA concentrations. That is, as the BPA concentration increases, the corresponding measured fluorescence decreases.

The analyzer of the present invention includes an aptamer having high selectivity such that bisphenol A, trace amounts of which is present in water, can be promptly measured in a field, and thus is a portable small-sized apparatus capable of simultaneously conducting all processes such as binding to bisphenol A, washing, separation, and measurement.

As used herein, the term "bisphenol A (BPA)" refers to a compound of the following Chemical Formula 1, which is used as a raw material for production of plastics such as polycarbonate or epoxy resin. Bisphenol A has been identified as a type of environmental hormone, and thus there is a need to effectively detect bisphenol A.

Chemical Formula 1

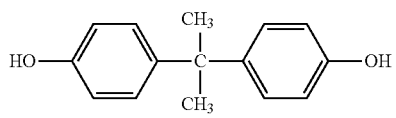

As used herein, the term "aptamer" refers to a type of polynucleotide consisting of a single-stranded nucleic acid (DNA, RNA, or modified nucleic acid) having a stable tertiary structure by itself and capable of binding to a target molecule with high affinity and specificity. The aptamer may use various substances such as a polynucleotide, a polypeptide, a compound, a polymer, etc., as a target molecule. In addition, the aptamer is superior in stability compared to protein, and synthesis thereof is easy because it consists of nucleic acids, and thus the aptamer is used in a method for detecting various target molecules.

In the present invention, the aptamer may be interpreted to mean an aptamer consisting of the nucleotide sequence of SEQ ID NO: 1 and capable of specifically binding to bisphenol A.

The aptamer having the nucleotide sequence of SEQ ID NO: 1 exhibits a simple two-dimensional structure as compared with a conventional aptamer, and thus may show an increased detection sensitivity to bisphenol A, which is a target material.

As used herein, the term "magnetic bead" is a magnetic material and, for the objects of the present invention, can form a complex bound to a first labeling material, an aptamer, and a second labeling material. If the magnetic bead can bind to a labeling material, a specific material, type, and amplitude of the magnetic bead can be used without limitation. The analyzer of the present invention further includes a magnetic force source located inside or outside the reaction vessel, and by collecting the magnetic beads, the detection of bisphenol A can be performed more accurately and easily.

As used herein, the term "labeling material" refers to a material generating a signal that be detected visually or by using a sensor. The signal may be generated by itself due to an inherent feature of the labeling material, such as luminescence, etc., but may also be generated by external stimulation, such as fluorescence.

In the present invention, the labeling material may be quantum dots, enzymes, colloid gold, electrochemical functional groups, fluorescence materials, radiolabels, fluorescent dye, or dyes, but is not particularly limited thereto.

The enzymes are not particularly limited as long as they can be used as labeling materials, but the enzymes may be horseradish peroxidase (HRP), alkaline phosphatase, glucose oxidase, luciferase, β-D-galactosidase, malate dehydrogenase (MDH), acetylcholinesterase, or analogues exhibiting similar activities thereto. In addition, the analogues may be nano-materials that produce $H_2O_2$.

Additionally, the fluorescent materials are also not particularly limited as long as they can be used as labeling materials, but the fluorescent materials may be fluorescein isothiocyanate, phycobiliproteins, 6-carboxyfluorescein, hexachloro-6-carboxyfluorescein, tetrachloro-6-carboxyfluorescein, 5-carboxyfluorescein (FAM), 2',4',5',7'-tetrachloro-6-carboxy-4,7-dichloroflorescein (HEX), cyanine-3 (Cy3), cyanine-5 (Cy5), 6-carboxytetramethylrhodamine, 5-carboxytetramethylrhodamine (TAMRA), black hole quencher 3 (BHQ3), etc.

The radiolabels are also not particularly limited as long as they can be used as labeling materials, but the radiolabels may be $^{125}I$, $^{131}I$, $^{14}C$, $^{3}H$, etc.

The present inventors have endeavored to detect and measure bisphenol A by measuring signals (lights) which vary depending on whether or not bisphenol A is bound.

In one embodiment of the present invention, the lights to be varied were converted into electrical charges (electrons), and the signal change due to the presence of bisphenol A was measured by values of the voltage drop of the feedback capacitor (or the voltage drop of the charge integrator output) (FIGS. 3 and 5a).

The analyzer of the present invention can detect bisphenol A by using a "first labeling material" and a "second labeling material". Specifically, the first labeling material binds to magnetic beads and is capable of emitting a certain signal irrespective of binding of bisphenol A. In addition, the second labeling material directly or indirectly binds to the aptamer before binding to bisphenol A. However, when bisphenol A present in samples binds to the aptamer, the second labeling material is separated from the aptamer.

In the present invention, bisphenol A may be detected by measuring signal changes of the first and second labeling materials according to the presence of bisphenol A.

In one specific aspect of the present invention, the present invention provides a portable analyzer for detecting bisphenol A, in which each of the first labeling material and the second labeling material is quantum dots, fluorescent dyes, radiolabels, or electrochemical functional groups.

As used herein, the term "first complex" may be a complex provided in the analyzer of the present invention before samples are injected, and may be a complex comprising the structure of the magnetic bead-first labeling material-aptamer-second labeling material. The first complex may be provided inside the reaction vessel of the analyzer of the present invention, but may be separately provided outside the reaction vessel. Additionally, the first complex may further comprise additional elements in order to facilitate detection and quantification of bisphenol A, but is not limited thereto.

As used herein, the term "second complex" is a complex formed when bisphenol A contained in samples reacts with the first complex. In addition, bisphenol A binds to the aptamer to form the second complex having the magnetic bead-first labeling material-aptamer-bisphenol A structure. In addition, the second labeling material bound to the aptamer is separated from the first complex due to the binding to bisphenol A, and thus is not included in the second complex. In other words, due to the presence of bisphenol A, the signal emitted from the second labeling material in the formation of the second complex is reduced.

In one specific aspect of the present invention, the first complex may be one provided inside the reaction vessel, but is not limited thereto.

As used herein, the term "reaction vessel" is a component of the analyzer of the present invention, in which the reaction of forming the second complex by reacting the first complex with bisphenol A is carried out. In one embodiment of the present invention, a cuvette is used for the reaction vessel. However, as long as the first complex and bisphenol A are allowed to react to form the second complex and the signal change caused thereby can be measured, any reaction vessel used in the art may be used without limitation. Vials of transparent materials (e.g., glass, plastic, etc.), microfluidics chips, strips, or various types of vessels may be used for the reaction vessel in the analyzer of the present invention, but the reaction vessel is not limited thereto.

In the present invention, the means for collecting the second complex refers to a means for separating the second complex from other materials, which did not form the second complex in the reaction vessel, through the process of collecting the second complex, which is formed by bisphenol A present in samples, into a certain region of the reaction vessel. Due to such separation of the second complex, more accurate detection of bisphenol A is possible by removing the signal emitted from the second labeling material which is separated according to the binding of bisphenol A. The method for collecting the second complex can be used without limitation as long as the second complex can be collected using the electrochemical properties, weight, size, etc. of the second complex. Additionally, the means for collecting the second complex may collect the second complex as well as the first complex, but the second labeling material separated from the first complex is not collected by the means above.

In one specific aspect of the present invention, the means for collecting the second complex may include a magnetic force source for applying a magnetic force to the reaction vessel in an ON/OFF manner so as to collect the second complex, but is not limited thereto.

When a magnetic force source is used in the means for collecting the second complex, by applying a magnetic force to the magnetic beads contained in the complex, only an intended complex can be collected in a specific region of the reaction vessel. Accordingly, it causes easy and accurate detection of the signal in washing and fluorescence measurement processes, which are conducted thereafter.

Additionally, in one specific aspect of the present invention, the reaction unit may further include (iv) a means for removing the first complex and bisphenol A, which did not form the second complex, and the separated second labeling material.

In the present invention, the signal emitted from materials other than the second complex may be removed by including the removing means.

Although the removing means is not limited to the method. However, the removing means specifically further includes:

a washing solution vessel comprising a washing solution; and a means for transporting the washing solution from the washing solution vessel to the reaction vessel to remove the first complex and bisphenol A, which did not form the second complex, and the separated second labeling material with the transported washing solution, but is not limited thereto. More specifically, the removal by the washing solution may be performed 1 time to 5 times.

In one embodiment of the present invention, the collection of the second complex and washing (e.g., rinsing) were performed using miniature peristaltic pumps and an articulated magnet. Specifically, the magnet was placed near the surface of a cuvette to collect the second complex while rinsing the cuvette with Tris-HCl buffer using the peristaltic pumps. In particular, it was confirmed that when the rinsing process was performed twice, the measured fluorescence signal was constant (FIG. 9c).

In one specific aspect of the present invention, the detection unit may further include a signal-generating means for generating a signal from the first and second labeling materials.

For the objects of the present invention, as long as a signal-generating means can generate a signal which can be recognized by the naked eye or sensors from the first and second labeling materials included in the first or second complex, the type or amplitude of a signal and a signal-generating method may be included in the signal-generating means of the present invention, without limitation. Specifically, the signal-generating means may include a light-emitting diode (LED), a laser diode (LD), a vertical-cavity surface-emitting laser, a semiconductor diode, or a mercury lamp, but is not limited thereto.

In one embodiment of the present invention, the analyzer of the present invention used an LED array as the signal-generating means; generated signals by inducing excitation of the first and second labeling materials; and measured the generated signals using a charge integrator (FIG. 1b).

In the present invention, the means for detecting signals generated from the labeling materials is not limited as long as the means can detect and measure the signals generated from the labeling materials. Specifically, the means for detecting the signals is not particularly limited as long as it can measure the concentration, amplitude, current or voltage, color, light quantity, pixel, etc. of the generated signals according to the type of the generated signals.

In one specific aspect of the present invention, the means for detecting signals generated from the labeling materials may be a photodiode and a charge integrator (or a charge amplifier), but is not limited thereto.

According to an embodiment of the present invention, the analyzer of the present invention includes a photodiode and a charge integrator for measuring an output from the photodiode. The photodiode generates a voltage drop of the feedback capacitor by converting signals, which are caused by the second labeling material and which are generated according to a combination of bisphenol A and the aptamer, into an electrical charge, and by accumulating the converted charge in the feedback capacitor. A user using the analyzer of the present invention can detect the presence of bisphenol A from the voltage drop generated and quantify the same. The output from the charge integrator is 0 V to 5 V, and can be read by the microcontroller board pins. In addition, the read values can be displayed on the LCD.

In one specific aspect of the present invention, the reaction unit may further include (v) a vibrating element for vibrating the reaction vessel. Specifically, the vibrating element may agitate the reaction vessel to prevent settling of the second complex, but is not limited thereto.

The analyzer of the present invention includes a power source to prevent settling of the complex formed in the process (incubation) of forming the second complex and the process (fluorescence measurement) of measuring the generated signals. As a result, the analyzer of the present invention is advantageous in that bisphenol A can be detected and quantified with higher sensitivity. The power source may be a vibrating element.

In one embodiment of the present invention, the present inventors have compared the results of incubation and fluorescence measurement in the cases where vibration is not applied and the case where vibration is applied. As a result, it was confirmed that in the presence of vibration, not only could the settling of the complex be prevented, but also fluorescence signals with a certain level could be obtained. Additionally, it was also confirmed from the above that the efficiency of the analyzer of the present invention for the detection of bisphenol A could be enhanced (FIGS. 7c and 8a).

In one specific aspect of the present invention, the detection unit may further include a calculation means for calculating the concentration of bisphenol A based on a change in the signal of the second labeling material for the detected first labeling material, but is not limited thereto.

In the analyzer of the present invention, the aptamer included in the first complex binds to bisphenol A, and thus the second labeling material is separated from the complex; therefore, bisphenol A can be detected and quantified by measuring the signal of the second labeling material, which is decreased due to the presence of bisphenol A.

In the calculation means of the present invention, by comparing the signals of the first and second labeling materials included in the first complex before the injection of samples and the signals of the first and second labeling materials of the second complex formed by bisphenol A contained in samples after the injection of the samples, not only can bisphenol A be detected, but it can also be quantified. That is, as the amount of bisphenol A is larger, the second labeling material is more separated from the first complex so that the signal generated from the second labeling material is reduced. Therefore, the amount of bisphenol A present in the samples can be calculated from the relative values of the first labeling material, which emits a constant signal regardless of the presence of bisphenol A.

In the calculation means of the present invention, the signals of the first and second labeling materials, which are generated in advance in the first complex before the introduction of samples, may each be set as reference values. Based on these reference values, a change in the signal generated after the introduction of bisphenol A in the samples can be measured.

In one specific aspect of the present invention, the detection unit may further include a means for outputting the concentration of bisphenol A, which is calculated by the calculation means, but is not limited thereto. The analyzer of the present invention may include the output means that is not limited in size or shape, but the output means may preferably be an LCD display window.

In one specific aspect of the present invention, the analyzer may further include a heat sink or a fan, but is not limited thereto.

In one specific aspect of the present invention, the analyzer may further include a control unit controlling the means for collecting the second complex, the signal-generating means, and the detection unit in an ON/OFF manner, but is not limited thereto.

In one embodiment of the present invention, the analyzer of the present invention was further provided with a control device capable of controlling the peristaltic pumps, servo motor and articulated magnet, vibrating motor, and LCD array, and thus the reaction performed in the analyzer of the present invention was adjusted as necessary (FIG. 6).

In an embodiment of the present invention, the present inventors produced and demonstrated a palm-sized analyzer capable of detecting bisphenol A at environmental concentrations (<1 ng/mL or ppb) (Example 1, FIGS. 1 and 2).

As a result of the baseline characterization experiment using empty cuvettes, quantum dots, and magnetic beads, the analyzer of the present invention showed that the concentrations of $QD_{565}$ and $QD_{655}$ could be measured at $10^{-3}$ µmol/L to $10^{-1}$ µmol/L, and $10^{-5}$ µmol/L to $10^{-1}$ µmol/L, respectively. The vibration of the cuvettes was useful not only in reducing the standard deviation of the signals measured in the fluorescence measurement process but also in preventing settling of the MB-QD-BPA complex that may occur during the incubation process.

Fluorescence measurement performance evaluation of the analyzer of the present invention was carried out by off-system incubation and rinsing in samples containing bisphenol A (0.0005 ng/mL to 1 ng/mL (ppb)). As a result of fluorescence measurement, without vibration, the linear regression curve was given as $y=-0.24 \log_{10}(x)+5.40$, $r^2=0.91$; and with vibration, the linear regression curve was given as $y=-0.15 \log_{10}(x)+5.76$, $r^3=0.75$. Fluorescence measurement on the same samples was performed via commercial spectrofluorometer with a correlation coefficient of $r=0.91$ with respect to that by the analyzer of the present invention.

In an embodiment of the present invention, an incubation duration of 30 minutes and a double rinse cycle were determined to be appropriate for on-system incubation and rinsing. Subsequent analysis of samples of bisphenol A (0.0005 ng/mL to 1 ng/mL, or ppb) using on-system incubation and analysis yielded the linear regression curve of $y=-0.20 \log_{10}(x)+2.32$, $r^2=0.89$ (without vibration) and $y=-0.21 \log_{10}(x)+2.81$, $r^2=0.90$ (with vibration).

The correlation coefficient between off-system and on-system incubation and rinsing (as measured by the commercial spectrofluorometer) was determined to be r=0.92. The correlation coefficient between bisphenol A detection by the analyzer of the present invention (with on-system incubation and rinsing) and the laboratory protocol (off-system incubation and rinsing with the commercial spectrofluorometer) was r=0.72.

The results above of the embodiment mean that the present inventors have demonstrated the possibility of implementing the equivalence of the laboratory protocol using the analyzer of the present invention (FIG. 10).

In another aspect of the present invention, the present invention provides a method for detecting bisphenol A using the portable analyzer for detecting bisphenol A, which includes injecting a collected sample into an inlet.

It is apparent that the definition of the terms described above and the constitution of the analyzer are identically applied to the method of the present invention for detecting bisphenol A.

A user who intends to detect and quantify bisphenol A in a field susceptible to contamination of bisphenol A can detect and identify the results in the field by using the portable analyzer of the present invention for detecting bisphenol A.

A user using the analyzer of the present invention i) may inject a sample collected in the field into the inlet so that the first complex provided in the reaction vessel of the analyzer of the present invention reacts with bisphenol A in the injected sample; or ii) may simultaneously or sequentially inject the first complex, which is provided separately, and the sample so that the injected first complex reacts with bisphenol A in the sample, but is not limited thereto.

In one specific aspect of the present invention, the present invention provides a method for detecting bisphenol A, in which the injection of the sample into the inlet is performed by simultaneously or sequentially injecting a collected sample; and a first complex including a magnetic bead, a first labeling material, a second labeling material, and an aptamer specifically binding to bisphenol A.

Advantageous Effects of the Invention

The portable analyzer of the present invention for detecting bisphenol A includes an aptamer capable of specifically detecting bisphenol A, and thus the analyzer does not require transport of the sample and can detect bisphenol A even in a contaminated environment, where bisphenol A is present at low concentrations, at a level similar to that detected in a laboratory.

BRIEF DESCRIPTION OF DRAWINGS

FIGS. 7a-7e are graphs illustrating the results of setting a baseline in the analyzer according to an embodiment of the present invention for detecting BPA. FIG. 7a is a graph illustrating the normalized output signal (CH2/CH1) of five individual empty reaction vessels. FIG. 7b is a graph illustrating the normalized output signal for the reagent volume in the reaction vessel. FIG. 7c is a graph illustrating the normalized output signal for both empty reaction vessel and Tris-HCl buffer-filled reaction vessel (with and without vibration). FIG. 7d is a graph illustrating the voltage gradient of $QD_{565}$ (CH1) and $QD_{655}$ (CH2) serially diluted in a Tris-HCl buffer, which was measured by the analyzer according to the present invention for detecting BPA. FIG. 7e is a graph illustrating the fluorescence of samples in which $QD_{565}$ and $QD_{655}$ are serially diluted in a Tris-HCl buffer, which was measured by the commercial spectrofluorometer.

FIG. 8a is a graph illustrating samples at 0, 5, 15, and 30 minutes without vibration (left) and with vibration (right). FIG. 8b is a graph illustrating the result of performing fluorescence measurement by the portable analyzer for detecting BPA without vibration. FIG. 8c is a graph illustrating the result of performing fluorescence measurement by the portable analyzer for detecting BPA with vibration. FIG. 8d is a graph illustrating the result of fluorescence measurement by the commercial spectrofluorometer. FIG. 8e is a graph illustrating fluorescence measurement correlation between the portable analyzer of the present invention for detecting BPA and the commercial spectrofluorometer.

FIGS. 9a-9c are graphs illustrating the normalized fluorescence of BPA (F655/F565) at three different concentrations (0.5 ng/mL, 1.0 ng/mL, and 5.0 ng/mL) according to the incubation times (5, 15, 30, and 45 minutes). FIG. 9a shows the result without vibration. FIG. 9b shows the result with vibration. FIG. 9c is a graph illustrating the normalized fluorescence according to the rinse cycle (1.0 ng/mL).

FIG. 10a is a graph illustrating the result of fluorescence measurement by the portable analyzer for detecting BPA without vibration. FIG. 10b is a graph illustrating the result of fluorescence measurement by the portable analyzer for detecting BPA with vibration. FIG. 10c is a graph illustrating the result of fluorescence measurement by the commercial spectrofluorometer. FIG. 10d is a graph illustrating the correlation between incubation and rinsing processes of off-system and on-system. FIG. 10e is a graph illustrating the correlation between the portable analyzer according to the present invention for detecting BPA and laboratory protocol (off-system incubation+rinsing+commercial spectrofluorometer).

DETAILED DESCRIPTION OF THE INVENTION

Hereinbelow, the present invention will be described in detail with accompanying exemplary embodiments. However, the exemplary embodiments disclosed herein are only for illustrative purposes and should not be construed as limiting the scope of the present invention.

Example 1: Design of Portable Analyzer for Detecting BPA

Figure 1A:
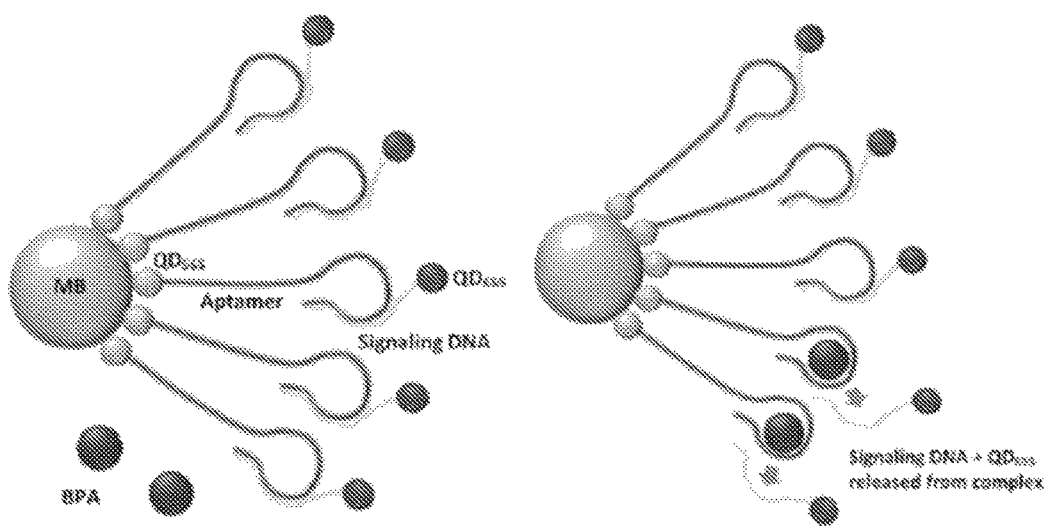
FIG. 1a is a diagram of a mechanism for detecting bisphenol A (BPA) in the portable analyzer of the present invention for detecting BPA. A complex containing an aptamer for detecting BPA is shown.
Figure 1B:
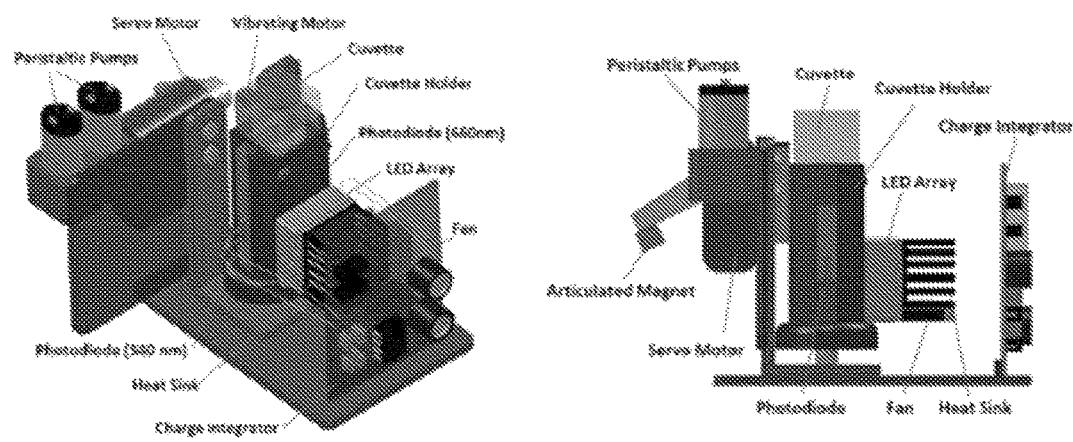
FIG. 1b is a diagram illustrating the portable analyzer for detecting BPA, which does not include the control unit according to an embodiment of the present invention.
Figure 2:
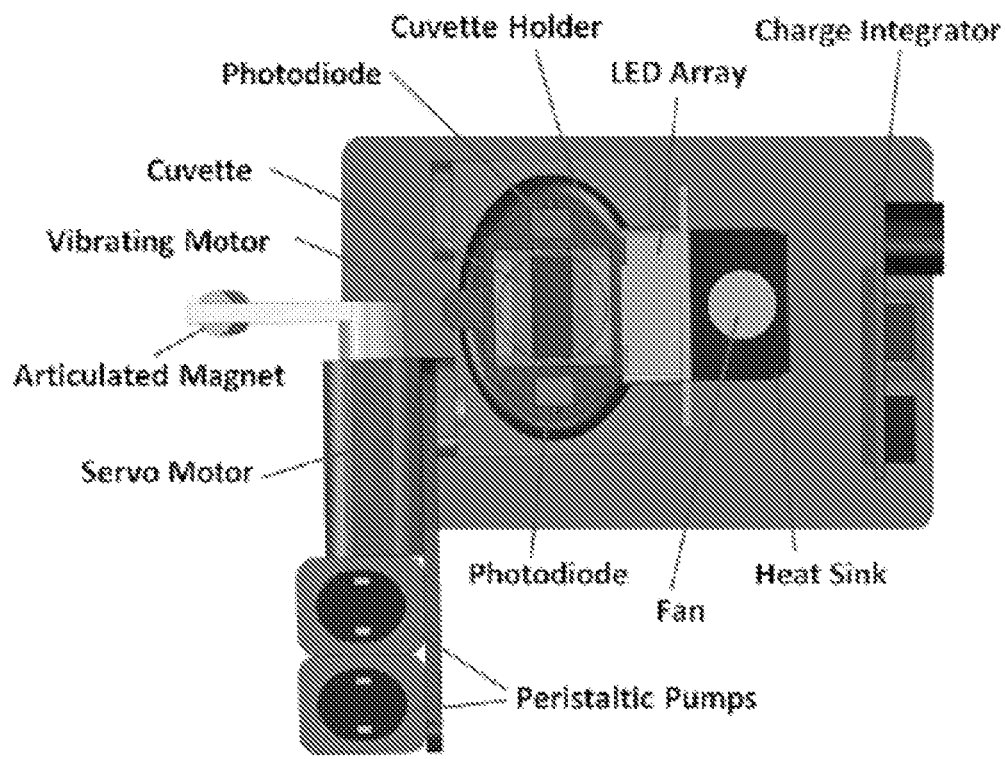
FIG. 2 is a plan view of the portable analyzer according to an embodiment of the present invention for detecting BPA.

The present inventors have tried to develop a portable analyzer for detecting BPA directly in a contaminated environment, and as a result, they have designed an analyzer including an aptamer capable of specifically detecting BPA, in which the reaction and analysis can be performed in a single reaction vessel (cuvette) (FIGS. 1 and 2).

The detection of BPA using the portable analyzer of the present invention for detecting BPA can be carried out in three steps: (i) incubation, (ii) rinsing, and (iii) fluorescence measurement. The components of the analyzer of the present invention are as follows:

The primary components of the analyzer consist of
(i) a cuvette holder;
(ii) miniature peristaltic pumps (Dolomite Miniature Peristaltic Pump, 3 V DC, 0.12 W, 0.45 mL/min, Dolomite Centre Ltd, Royston, UK) for transferring reagents;
(iii) an articulated magnet (Neodymium, D42-N52, Disc ¼"×⅛", K&J Magnetics Inc, Pennsylvania, USA) mounted on a servo motor (TowerPro SG90 Servo, 4.8 V, Taiwan);
(iv) a vibrating motor (Model Z7AL2B1690002, up to 12,000 rpm, Jinlong Machinery and Electronics Co. Ltd, China) for reagent agitation;
(v) an LED array (10 W, 400 nm to 405 nm, Epiled, China) for excitation of quantum dots;
(vi) a pair of photodiodes for detection (S6430-01 and S6429-01, Hamamatsu Photonics K.K., Japan); and
(vii) a charge integrator to measure the output from the photodiodes. The LED array is further fitted with a heat sink and fan to prevent overheating.

Figure 5A:
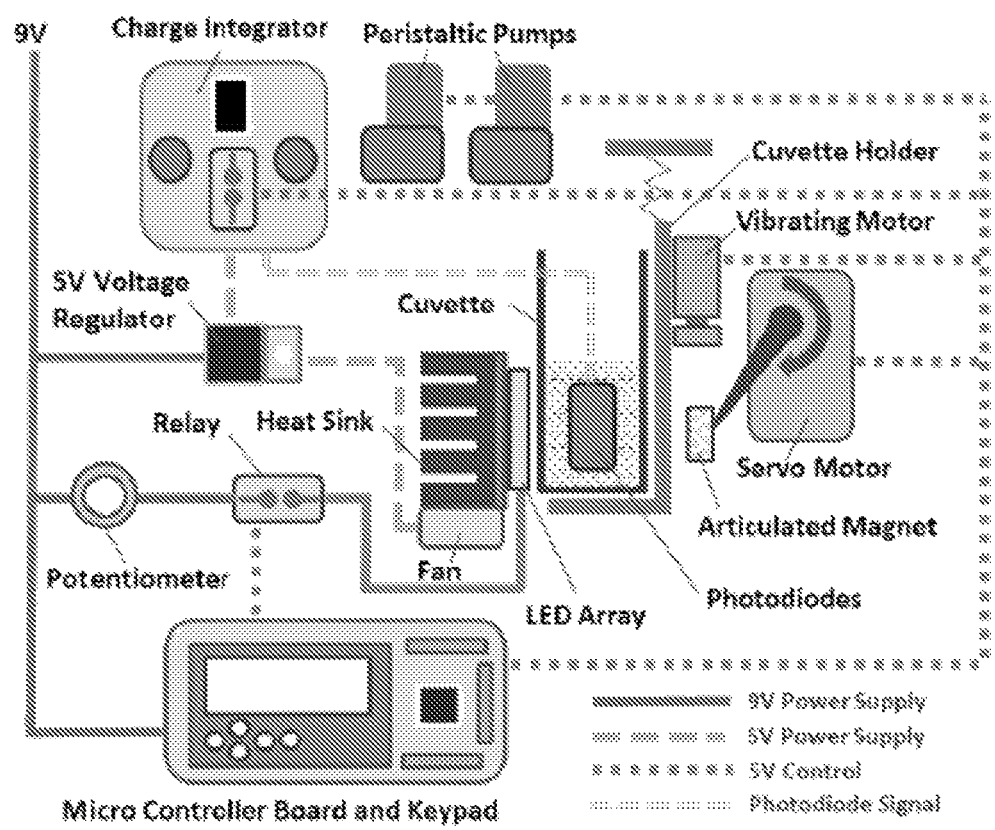
FIG. 5a is an operation schematic of the portable analyzer according to an embodiment of the present invention for detecting BPA.

Additionally, the components may be controlled by an Arduino compatible Mega2560 microcontroller board via a 16×2 LCD and key pad (FIG. 5a).

Figure 3:
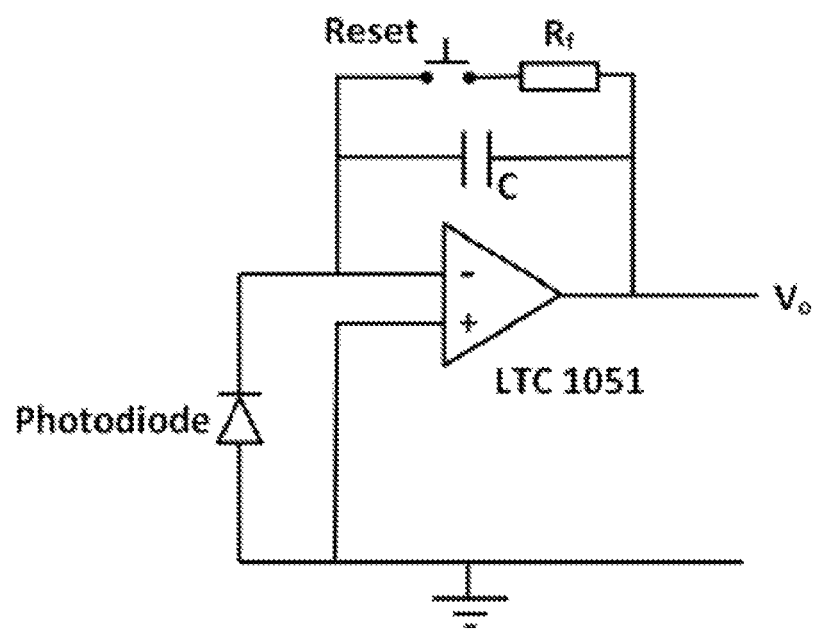
FIG. 3 is a schematic diagram of the charge integrator according to an embodiment of the present invention.
Figure 4:
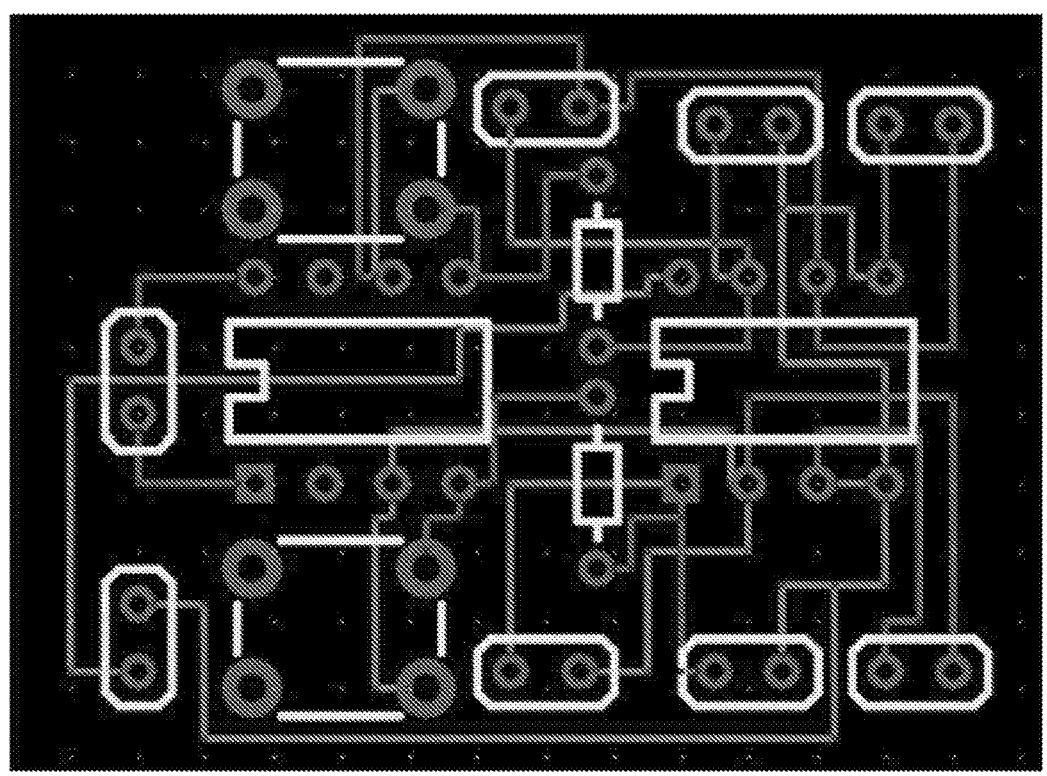
FIG. 4 is a diagram illustrating a PCB layout of the charge integrator according to an embodiment of the present invention.

The charge integrator was custom-designed and manufactured. It was designed by including a low cost precision operational amplifier (LTC1051, Linear Technologies, USA), a 10 μF feedback capacitor, and 2 kΩ feedback resistor (FIGS. 3 and 4).

The photodiodes in the charge integrator were used to convert signals, which are changed depending on whether BPA and the aptamer are bound, into electrical charges (electrons), and the converted electrical charges were accumulated in a feedback capacitor to generate a voltage drop of the feedback capacitor (or the voltage drop of the charge integrator output).

The output of the charge integrator was 0 V to 5 V, and the outputted voltage was recorded using a data logger (PCS10, 4-Channel Recorder, Velleman, UK). The voltage outputs of the 540 nm and 660 nm photodiodes (via the charge integrator) were recorded by the data recorder as CH1 and CH2, respectively.

The measured normalized output signal of the portable analyzer for detecting BPA was calculated as follows:

$$\text{Normalized output signal} = \frac{\text{Voltage gradient of } CH2}{\text{Voltage gradient of } CH1}$$

The voltage gradient was calculated by dividing the change in output voltage from the charge integrator over the time duration.

The LED array for quantum dot excitation was powered via a parallel 9 V line with a serial potentiometer. The potentiometer determined the final voltage of the LED array, and the 9 V line (a 5 V voltage regulator; LM7805A, Fairchild Semiconductor, USA) supplied power to both the fan and charge integrator. Electrical relays (TQ2-5V, Matsushita Electric Works, Japan) were used for switching the LED array as well as resetting the charge integrator.

Figure 6:
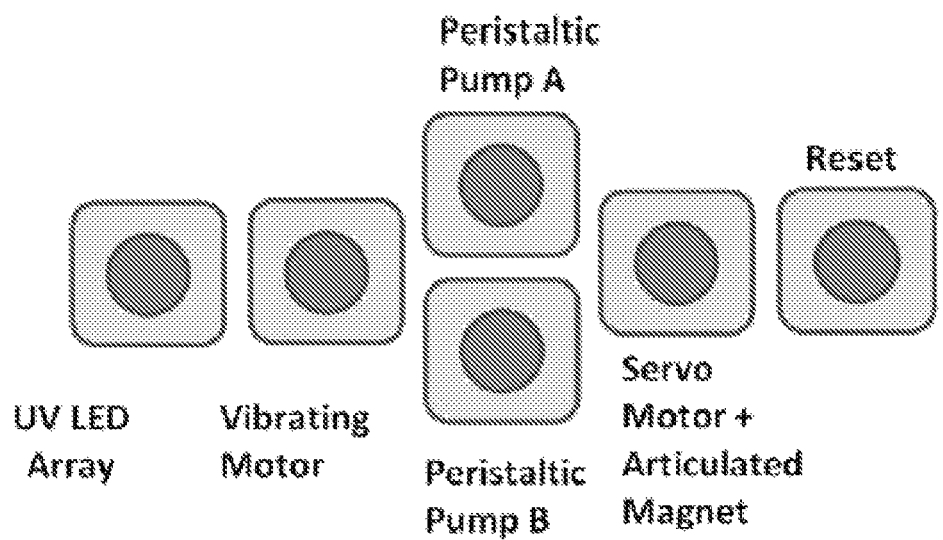
FIG. 6 is a diagram illustrating the control unit according to an embodiment of the present invention.

During operation of the analyzer of the present invention, the user controlled the peristaltic pumps, servo motor and articulated magnet, vibrating motor, and LCD array via the control unit (FIG. 6).

A vibration motor was used to maintain homogeneity of the samples during the incubation as well as the fluorescence measurement. The agitation using the vibration motor can be easily facilitated by suspending the reaction vessel (cuvette) holder from a plastic pivot. During the fluorescence measurement, a cap was placed on the cuvette to minimize background light.

Figure 5B:
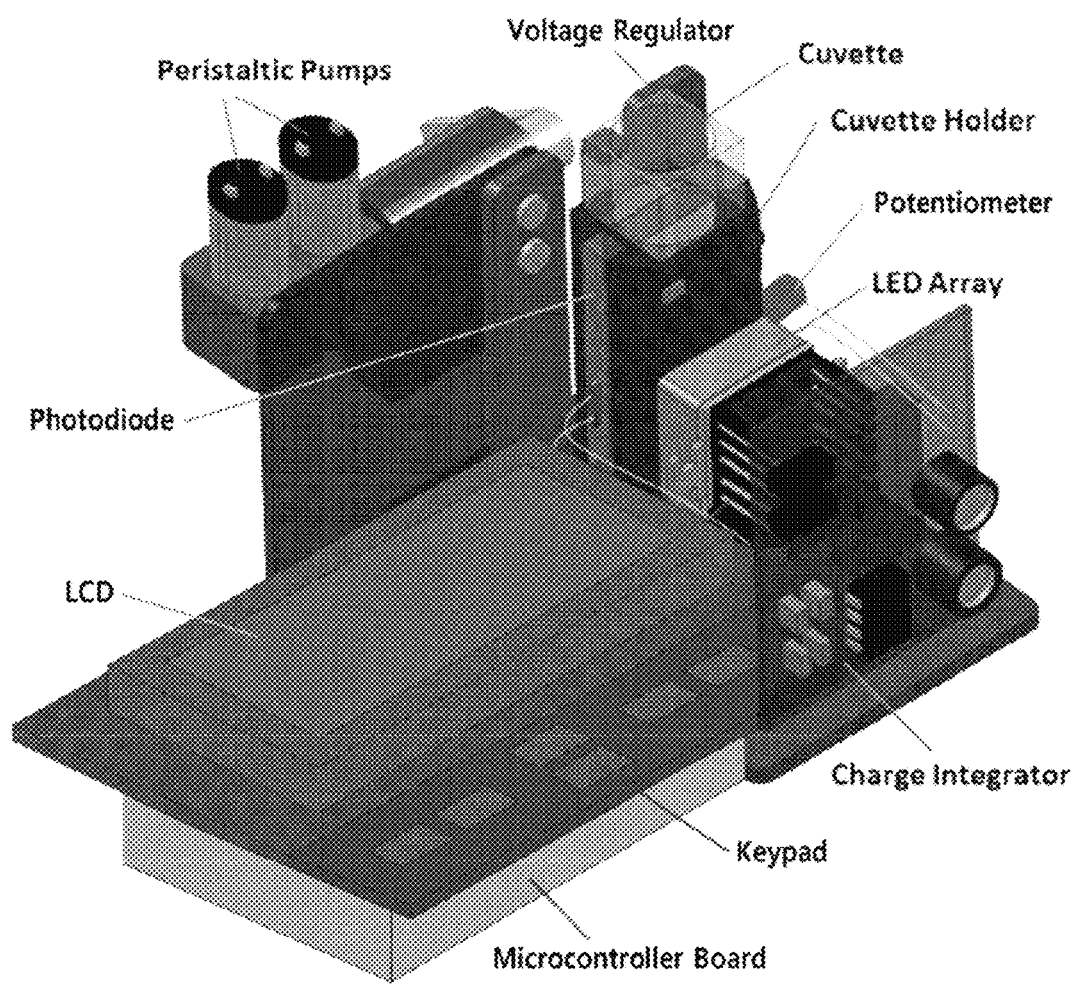
FIG. 5b is a drawing of the portable analyzer according to an embodiment of the present invention for detecting BPA.

The NanoAptamer analyzer according to the present invention, which has the above-described constitution, is a small-sized device, the size of which is similar to the size of the palm of a hand (FIG. 5b).

Example 2: Characterization of Baseline of Portable Analyzer for Detecting BPA Baseline characterization of the portable analyzer for detecting BPA was necessary to establish the operational limits of the analyzer prior to actual BPA detection and quantification. Accordingly, the present inventors performed the baseline characterization experiment in the following steps:
(i) Response of empty cuvettes during fluorescence measurement
(ii) Response with various reagent volumes (Tris-HCl buffer)
(iii) Cuvette vibration during fluorescence measurement
(iv) Fluorescence measurement of quantum dots only ($QD_{565}$ and $QD_{655}$)
(v) Cuvette vibration to minimize settling of complexes
(vi) Fluorescence measurement of MB-$QD_{565}$ complex only The steps above will be described in more detail as follows:

Example 2-1: Response of Empty Cuvettes During Fluorescence Measurement

In the Example, the present inventors used UV/visible range semi-micro cuvettes (Kartell®, Millan, Italy). Since the cuvettes were made of polymethylmethacrylate (PMMA), individual cuvettes might have slight changes, which in turn cause variations during fluorescence measurement.

Therefore, background optical characterization of empty cuvettes was required to be performed before using the analyzer of the present invention.

To do this, five different empty cuvettes were inserted into the analyzer of the present invention, and the fluorescence measurement step (three times per cuvette) was performed. The fluorescence measurement step consisted of illumination by a UV-LED and measurement by photodiodes. The voltage outputs of 540 nm and 660 nm photodiodes (via the charge integrator) were recorded by a data recorder (PCS10, 4-Channel Recorder, Velleman, UK) as CH1 and CH2, respectively. The normalized output signals were calculated and compared.

Example 2-2: Response with Various Reagent Volumes

Additionally, in order to determine the optimized reagent volume in the cuvette for fluorescence measurement for the detection of BPA, the present inventors prepared cuvettes filled with a Tris-HCl buffer (0.02 mol/L, pH 8, 0.005% SDS).

The Tris-HCl buffer consisted of 0.02 mol/L of Tris-HCl (Sigma-Aldrich Co., St. Louis, USA), 0.02 mol/L of $MgCl_2.6H_2O$ (Daejung, Gyung-gi, Korea), 0.04 mol/L of KCl (Duksan, Gyung-gi, Korea), and 0.1 mol/L of NaCl (Junsei, Tokyo, Japan). Additionally, sodium dodecyl sulfate (SDS, Sigma-Aldrich Co.) was added to the Tris-HCl buffer (0.02 mol/L, pH 8) so that the final concentration reached 0.005% (V/V). Cuvettes containing various volumes of the Tris-HCl buffer (0.02 mol/L, pH 8, 0.005% SDS) between 100 µL and 1000 µL were inserted into the analyzer of the present invention to perform fluorescence measurement and the normalized output signals were compared.

Example 2-3: Confirmation of Effect of Cuvette Vibration During Fluorescence Measurement In order to confirm the background effect of cuvette vibration during fluorescence measurement by the analyzer of the present invention, an empty cuvette and a Tris-HCl buffer (1000 µL)-filled cuvette were compared. Fluorescence measurement was performed with and without vibration (in triplicate), and the normalized output signals obtained were compared.

Example 2-4: Fluorescence Measurement of Quantum Dots Only

In order to confirm the fluorescence measurement range of the analyzer of the present invention, the present inventors used serially diluted quantum dots in the Tris-HCl buffer.

Specifically, commercial carboxyl quantum dots $QD_{565}$ and $QD_{655}$ (Invitrogen, Carlsbad, USA) were procured as an 8 µM stock. The test samples used in the Example had a volume of 1000 µL (in cuvettes) with a final QD concentration of $10^{-1}$ µmol/L to $10^{-6}$ µmol/L.

The test samples were subjected to fluorescence measurement by both the analyzer of the present invention and a commercial spectrofluorometer (Molecular devices, SpectroMax M2 microplate reader, Sunnyvale, USA). The excitation and emission wavelengths of the quantum dots were 360 nm and 570 nm for $QD_{565}$, and 360 nm and 660 nm for $QD_{655}$, respectively.

Example 2-5: Confirmation of Effect of Cuvette Vibration to Minimize Settling of Complexes In order to minimize settling due to the weight of magnetic beads of the complexes during incubation or fluorescence measurement, a vibrating element capable of vibrating cuvettes was included in the analyzer of the present invention.

The samples (200 µL) were each incubated for 0 minutes, 5 minutes, 15 minutes, and 30 minutes with and without vibration caused by the vibrating element. Post-incubation photographs were taken to compare the degree of settling.

Example 2-6: Fluorescence Measurement of $MB-QD_{565}$ Complex Only

Since magnetic beads were significantly larger and heavier than quantum dots, these may interfere fluorescence measurement of the analyzer of the present invention. Therefore, the present inventors examined fluorescence measurement in the presence of magnetic beads.

Specifically, the aminated magnetic beads (MB, Invitrogen) were covalently bonded with carboxylated $QD_{565}$ to form an $MB-QD_{565}$ complex. The complex was diluted with the Tris-HCl buffer to a final volume of 1000 µL. Fluorescence measurement by the analyzer of the present invention was performed on three test samples with the same complex in triplicate with and without vibration.

Example 3: Detection and Quantification of BPA by Portable Analyzer for Detecting BPA The capability of the analyzer of the present invention to detect and quantify BPA was demonstrated through the following steps.
(i) On-system fluorescence measurement of MB-QD-BPA complex (off-system incubation and rinsing)
(ii) Optimization of on-system incubation duration
(iii) Optimization of on-system rinsing cycle
(iv) On-system incubation, rinsing, and fluorescence measurement The steps above will be described in more detail as follows:

Example 3-1: Fluorescence Measurement of MB-QD-BPA Complex (Off-System Incubation and Rinsing)

The $MB-QD_{565}$-aptamer-$QD_{655}$ complex was prepared using the BPA-specific aptamer (24 bp, $NH_2-C_6-T_{10}$-GGA-TAGCGGGTTCC, SEQ ID NO: 1).

Specifically, the signaling probe (30 bp, $NH_2-C_6-T_{10}$-TATCCCACCTGACCACCCAC, SEQ ID NO: 2) labeled with $QD_{655}$ was hybridized with the $MB-QD_{565}$ complex prior to incubation with BPA.

BPA was dissolved in methanol (Duksan, Korea) as a stock solution. Thereafter, the BPA stock solution was serially diluted in deionized water to achieve various concentrations of 0 ng/mL to 1.0 ng/mL (ppb).

The prepared $MB-QD_{565}$-aptamer-$QD_{655}$ complex was incubated with BPA with the concentrations of 0 ng/mL, 0.0005 ng/mL, 0.001 ng/mL, 0.01 ng/mL, 0.1 ng/mL, and 1.0 ng/mL (ppb) on a bench shaker (Eppendorf, MixMate, Hamburg, Germany) for 2 hours to utlimately form a MB-QD-BPA complex.

After incubation, the formed MB-QD-BPA complex was manually separated using a magnet (Invitrogen, DynaMag™-2) and rinsed with the Tris-HCl buffer to form samples (test samples) with a volume of 200 µL.

The test samples prepared in the above were measured by the commercial spectrofluorometer (SpectraMax M2 microplate reader, Molecular Devices, CA, USA). This would also verify the successful completion of the reaction.

Further, for fluorescence measurement by the analyzer of the present invention, the test samples were diluted 5-fold with the Tris-HCl buffer to prepare samples having a final volume of 1000 μL.

Example 3-2: Optimization of On-System Incubation Duration

In order to optimize the duration for on-system incubation by the analyzer of the present invention, test samples with three different concentrations of BPA (i.e., 0.5 ng/mL, 1.0 ng/mL, and 5.0 ng/mL, or ppb) were prepared. At each concentration, the test samples were incubated for 5 minutes, 15 minutes, 30 minutes, and 45 minutes with and without vibration.

After incubation, the test samples were subjected to fluorescence measurement via the commercial spectrofluorometer (SpectraMax M2 microplate reader) at the wavelengths of 360 nm for excitation and 570 nm ($QD_{565}$) or 660 nm ($QD_{655}$) for emission. The results were presented as normalized fluorescence, which is given by the following equation:

$$\text{Normalized fluorescence} = \frac{\text{Fluorescence of } QD655}{\text{Fluorescence of } QD565}$$

Example 3-3: Optimization of On-System Rinsing Cycle

Four samples with the same amount of BPA (1.0 ng/mL or ppb) were prepared and incubated on-system for 30 minutes.

After on-system incubation, on-system rinsing was performed via miniature peristaltic pumps and an articulated magnet.

Specifically, the cuvette was rinsed with the Tris-HCl buffer using peristaltic pumps while the magnet was deployed to the near-surface of the cuvette to collect the MB-QD-BPA complexes. After each rinse, the complexes were re-suspended via vibrating the cuvette. Single and double rinse cycles were performed and the resulting normalized fluorescence was measured and compared.

Example 3-4: On-System Incubation, Rinsing, and Fluorescence Measurement

In this Example, the capability of the analyzer of the present invention to perform on-system incubation, rinsing, and fluorescence measurement was demonstrated.

First, the MB-QD complex was prepared in the same manner as in the Example above. The prepared complex was incubated with BPA of 0 ng/mL, 0.0005 ng/mL, 0.001 ng/mL, 0.01 ng/mL, 0.1 ng/mL, and 1.0 ng/mL (ppb) for 30 minutes in the reaction vessel of the analyzer of the present invention by exerting vibration.

After incubation, the articulated magnet and miniature peristaltic pumps were operated to transport the Tris-HCl buffer to the reaction vessel in which the reaction had been carried out, and then a double rinse cycle was performed.

After rinsing, the complex was diluted 5-fold to a final volume of 1000 μL prior to fluorescence measurement. The normalized output signal by the analyzer of the present invention was compared with that by the commercial spectrofluorometer.

The results of the experiments according to the Example above were analyzed as in the following Experimental Examples.

Experimental Example 1: Baseline Characterization of Portable Analyzer for Detecting BPA

Experimental Example 1-1: Response of Empty Cuvettes During Fluorescence Measurement The average normalized output signal and standard deviation of five individual empty cuvettes ranged from 0.5561 to 0.5986 and 0.0007 to 0.0025, respectively (FIG. 7a). That is, more variation was observed between individual empty cuvettes than repeated fluorescence measurement by the analyzer of the present invention.

Experimental Example 1-2: Response Result with Various Reagent Volumes

It was confirmed that when the reagent volume was less than 600 μL, the normalized output signal obtained as a result of fluorescence measurement fluctuated (FIG. 7b).

However, it was confirmed that when the reagent volume was increased beyond 600 μL, the output signal results had a relatively constant value (0.5628+0.0037).

Therefore, in order to obtain consistent fluorescence measurement results, fluorescence measurement of the analyzer of the present invention was performed using the reagent volume (1000 μL) in the following Examples. Since the reagent volume in which the reaction occurred in the reaction vessel of the analyzer was 200 μL, the reagent volume was diluted 5-fold, prior to fluorescence measurement by the analyzer of the present invention.

Experimental Example 1-3: Confirmation of Influence of Cuvette Vibration During Fluorescence Measurement The present inventors tried to confirm influence of the presence of vibration of cuvettes during fluorescence measurement. As a result, empty cuvettes showed normalized output signals at 0.5510 and 0.5776 for vibration-off and vibration-on, respectively (FIG. 7c and Table 1).

TABLE 1

| Normalized output signals of empty cuvettes and Tris-HCl buffer-containing cuvettes | | |
|---|---|---|
| CH2/CH1 | MEAN | STD |
| Empty cuvette (without vibration) | 0.5510 | 0.0033 |
| Empty cuvette (with vibration) | 0.5776 | 0.0018 |
| Tris-HCl buffer (without vibration) | 0.5460 | 0.0030 |
| Tris-HCl buffer (with vibration) | 0.5561 | 0.0011 |

For the cuvettes filled with the Tris-HCl buffer, the results were similar at 0.5460 and 0.5561. As expected, the standard deviation for the empty cuvette with vibration (at 0.0018) was lower than that without vibration (at 0.0033).

A similar trend was observed with the Tris-HCl buffer-filled cuvettes. Specifically, it was confirmed that the standard deviation for the output signal of the Tris-HCl buffer-filled cuvette with vibration was at 0.0011, which was lower than that for the output signal of the Tris-HCl buffer-filled cuvette without vibration (at 0.0030).

It was confirmed from the results above that when vibration was applied to the reaction vessel during the fluorescence measurement process for detecting BPA, the standard deviation of the measured output signals was reduced.

Experimental Example 1-4: Fluorescence Measurement of Quantum Dots Only

Concentrations of $QD_{565}$ and $QD_{655}$ were measured with the portable analyzer of the present invention for detecting BPA, and the results were confirmed as voltage gradients.

As a result, it was confirmed that the concentrations of the quantum dots $QD_{565}$ and $QD_{655}$ were from $10^{-3}$ mol/L to $10^{-1}$ μmol/L and $10^{-5}$ μmol/L to $10^{-1}$ μmol/L, respectively (FIG. 7d).

At each concentration within the measurement range, $QD_{655}$ exhibited a higher voltage gradient (fluorescence) than $QD_{565}$. The linear regression curve for $QD_{565}$ was given as $\log_{10}(y)=0.55 \log_{10}(x)+0.59$ ($r^2=0.96$) for a concentration range of $10^{-3}$ μmol/L to $10^{-1}$ μmol/L. Further, the linear regression curve for $QD_{655}$ was given as $\log_{10}(y)=0.64 \log_{10}(x)+1.68$ ($r^2=0.95$) for a concentration range of $10^{-5}$ μmol/L to $10^{-1}$ μmol/L.

As expected by the present inventors, fluorescence measurement of the same samples by a commercial spectrofluorometer yielded steeper linear regression slopes compared to the analyzer of the present invention (FIG. 7e). The linear regression curve for $QD_{565}$ was given as $\log_{10}(y)=1.0 \log_{10}(x)+5.33$ ($r^2=0.999$) for a concentration range of $10^{-4}$ μmol/L to $10^{-1}$ μmol/L. The linear regression curve for $QD_{655}$ was given as $\log_{10}(y)=1.03 \log_{10}(x)+5.99$ ($r^2=0.997$) for a concentration range of $10^{-5}$ μmol/L to $10^{-1}$ μmol/L.

Experimental Example 1-5: Cuvette Vibration to Minimize Settling of Complexes

Figure 8A:
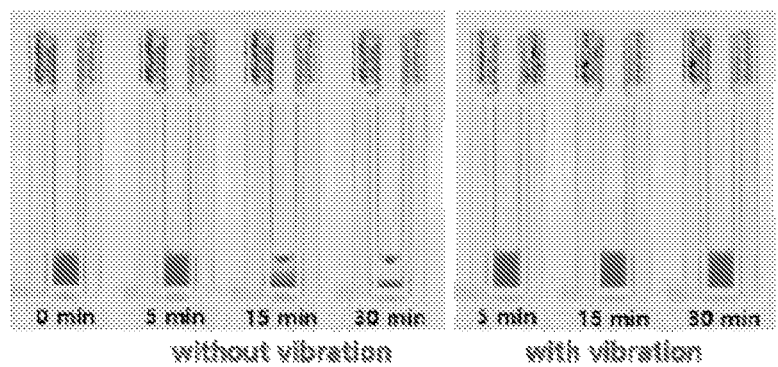
FIGS. 8a-8e are graphs illustrating the results after incubation and rinsing processes in a laboratory environment, not in the portable analyzer according to the present invention for detecting BPA.

After conducting incubations with and without vibration, the degree of settling of the samples was compared (FIG. 8a).

Using 0 minutes as a negative control, no significant difference was observed in the settling of the samples during the incubation time (5 minutes). However, for the sample incubated for 15 minutes, settling of the complexes became apparent in the absence of vibration. In addition, after 30 minutes, it was confirmed that the settling was completed and that the supernatant liquid became transparent.

From these results, the present inventors confirmed that when BPA was detected using the analyzer of the present invention, the incubation and fluorescence measurement can be facilitated by vibrating the reaction vessel, and as a result, the efficiency of the analyzer for detecting BPA could be increased.

Experimental Example 1-6: Fluorescence Measurement of $MB-QD_{565}$ Complex Only The three test samples including the $MB-QD_{565}$ complex exhibited the normalized output signals that are similar to each other (Table 2). The total average values that corresponded to with and without vibration are 0.4610 and 0.4527. With vibration, the standard deviation ranged from 0.0016 to 0.0042. Such standard deviation was smaller than that without vibration, where it ranged from 0.0034 to 0.0123. Fluorescence measurement with vibration showed a reduced standard deviation compared to that without vibration.

Such results seemed to be exhibited because the vibration applied to the reaction vessel prevented the aggregation and settling of the $MB-QD_{565}$ complex in the samples, thereby allowing more consistent fluorescence measurement.

TABLE 2

The normalized output signals (CH2/CH1) of the $MB-QD_{565}$ complex, which are measured through the portable analyzer for detecting BPA without and with vibration

| CH2/CH1 | 1 | 2 | 3 | Average | std |
|---|---|---|---|---|---|
| Without vibration | | | | | |
| #1 | 0.4652 | 0.4598 | 0.4546 | 0.4599 | 0.0053 |
| #2 | 0.4637 | 0.4597 | 0.4570 | 0.4601 | 0.0034 |
| #3 | 0.4504 | 0.4382 | 0.4258 | 0.4382 | 0.0123 |
| Average | | | | 0.4527 | 0.0129 |
| With vibration | | | | | |
| #1 | 0.4665 | 0.4721 | 0.4730 | 0.4705 | 0.0035 |
| #2 | −0.4611 | 0.4652 | 0.4695 | 0.4653 | 0.0042 |
| #3 | 0.4491 | 0.4461 | 0.4465 | 0.4472 | 0.0016 |
| Average | | | | 0.4610 | 0.0110 |

Experimental Example 2: Detection and Quantification of BPA Using Portable Analyzer for Detecting BPA Experimental Example 2-1: Fluorescence Measurement of MB-QD-BPA Complex (Off-System Incubation and Rinsing)

Figure 8B:
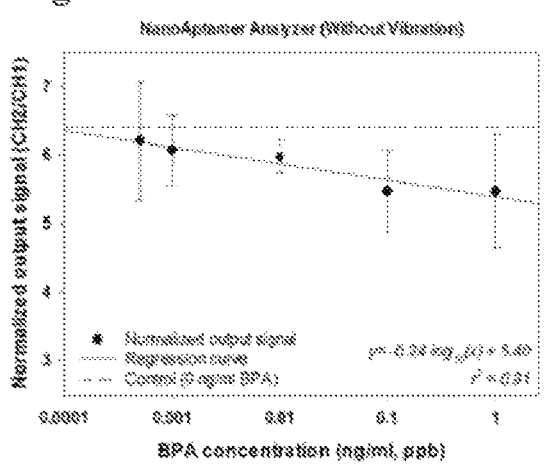
Figure 8C:
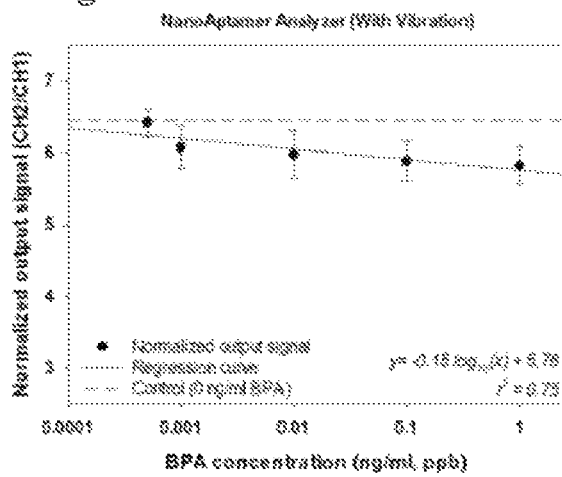
Figure 8D:
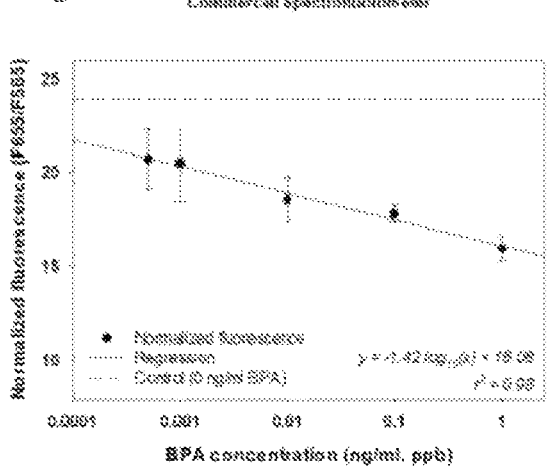

BPA (0.0005 ng/mL to 1 ng/mL (ppb)) of the samples, which were subjected to off-system incubation and rinsing was detected and quantified by using the portable analyzer of the present invention (FIGS. 8b and 8c). The linear regression curve of the resulting normalized output signal was given as $y=-0.24 \log_{10}(x)+5.40$, $r^2=0.91$, when vibration was not present. The linear regression curve thereof was given as $y=-0.15 \log_{10}(x)+5.76$, $r^2=0.75$, when vibration was present.

Similar to the results of the Examples above, the fluorescence measurement values in the presence of vibration showed significantly smaller standard deviation compared to those without vibration. The lower $r^2$ in the presence of vibration was attributable to the measurement at 0.0005 ng/mL (ppb).

The results of measuring fluorescence by the analyzer of the present invention were consistent with the results measured by a commercial spectrometer. The linear regression curve measured with a commercial spectrofluorometer was $-1.42 \log_{10}(x)+16.08$ with $r^2=0.98$.

Figure 8E:
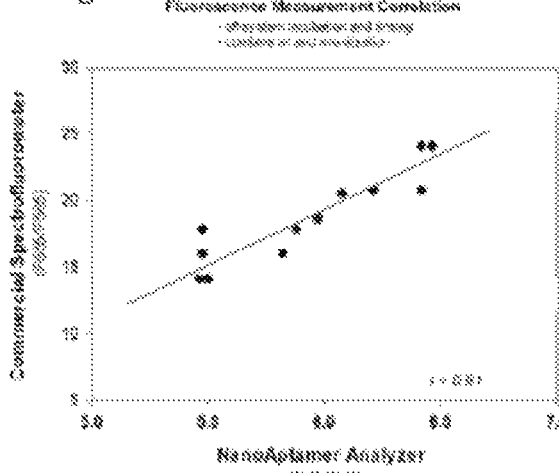

The fluorescence measurement correlation between the analyzer of the present invention and the commercial spectrofluorometer was confirmed using samples which were subjected to the same off-system (laboratory) incubation and rinsing processes (FIG. 8e). The correlation coefficient r was 0.91.

From the results above, the present inventors confirmed that the results obtained with the analyzer of the present invention were the same as the results of measuring fluorescence by the commercial spectrofluorometer, and that the analyzer of the present invention was able to detect BPA at an equivalent level compared to that detected in a laboratory environment.

Experimental Example 2-2: Optimization of On-System Incubation Duration

For incubation with vibration, a minimum of 30 minutes was required for sufficient incubation (red dotted box in FIG. 9b). As the BPA concentration increased, the normalized fluorescence was reduced.

However, in the absence of vibration, the trend according to the reaction was not observed even after 45 minutes (FIG. 9a).

From the results above, it was confirmed that when BPA was detected using the analyzer of the present invention, successful BPA detection was able to be performed due to the prevention of the settling of the complexes by exerting vibration.

Experimental Example 2-3: Optimization of On-System Rinsing Cycle

The present inventors tried to confirm a rinse cycle optimized for the detection of BPA using the analyzer of the present invention.

As a result, it was confirmed that the normalized fluorescence by a double rinse cycle showed more consistent results as compared to that by a single rinse cycle (FIG. 9c). In particular, samples #2, #3, and #4 showed similar results at 2.771 (+0.877) after the double rinse cycle.

Therefore, the double rinse cycle was used for subsequent on-system rinsing.

Figure 10A:
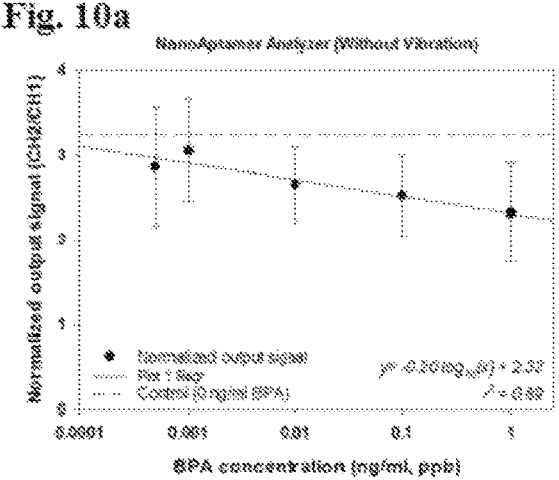
FIGS. 10a-10e are graphs illustrating the results after incubation and rinsing processes conducted in the portable analyzer according to the present invention for detecting BPA.
Figure 10B:
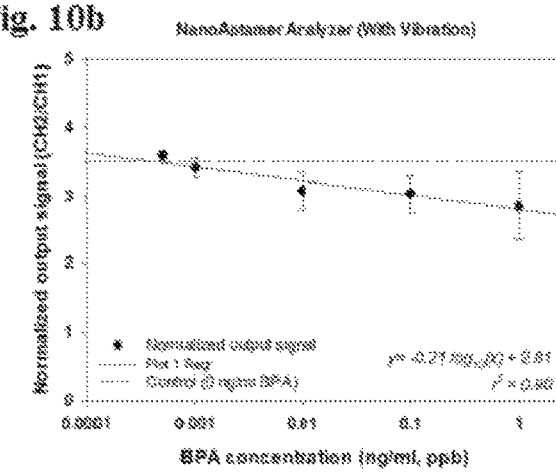

Experimental Example 2-4: On-System Incubation, Rinsing, and Fluorescence Measurement As a result of measuring on-system incubation, rinsing, and fluorescence using the analyzer of the present invention, it was confirmed that the samples showed a reaction similar to that when the samples were subjected to off-system incubation and rinsing (FIGS. 10a and 10b).

In the absence of vibration, the linear regression curve was given as $y=-0.20\ \log_{10}(x)+2.32$, $r^2=0.89$; and in the presence of vibration, the linear regression curve was given as $y=-0.21\ \log_{10}(x)+2.81$, $r^2=0.90$.

Figure 10C:
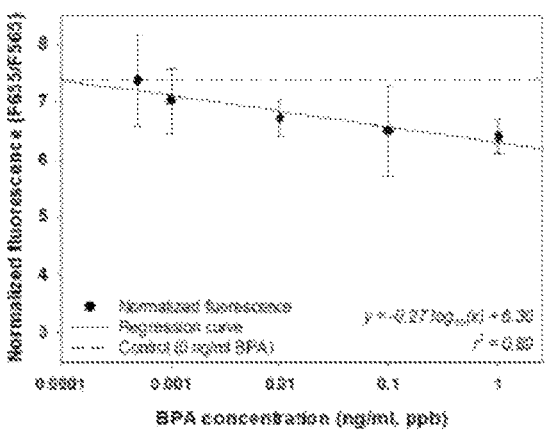

As expected, the standard deviation of fluorescence measurement in the presence of vibration was significantly smaller than that in the absence of vibration. FIG. 10c shows the normalized fluorescence of the same on-system incubated and rinsed samples measured by the commercial spectrofluorometer. Such fluorescence exhibited a linear regression curve given as $y=-0.27\ \log_{10}(x)+6.30$, $r^2=0.89$.

Figure 10D:
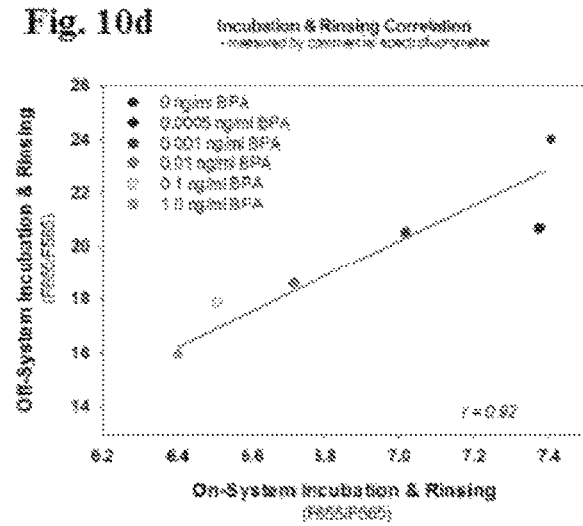

In order to establish equivalence between on-system and off-system incubation as well as rinsing, the correlation was investigated (FIG. 10d). In both cases, fluorescence measurement was performed using the commercial spectrometer. As a result, for the BPA concentration ranging from 0.0005 ng/mL to 1 ng/mL (ppb), the correlation coefficient for both off-system and on-system incubation and rinsing was r=0.92.

Figure 10E:
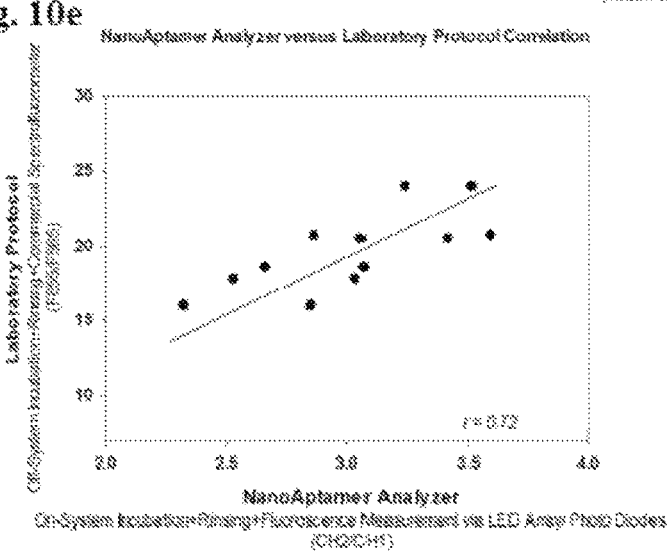

Finally, the present inventors compared the results of the BPA detection and quantification measured by using the laboratory protocol (off-system incubation+rinsing+commercial spectrometer) with those measured by using the analyzer of the present invention (on-system incubation+fluorescence measurement via LED array/photo diodes). As a result, it was confirmed that the correlation coefficient was r=0.72 (FIG. 10e).

From the results of the Examples above, it was confirmed that the results of incubating and rinsing the samples in the analyzer of the present invention were similar to those of performing the same with the laboratory protocol.

It was also confirmed that BPA was able to be sufficiently detected by incubating the collected samples and measuring fluorescence by the miniaturized analyzer of the present invention.

That is, the results indicate that the analyzer of the present invention can replace the existing laboratory protocol, and that a system capable of detecting and quantifying BPA at environmentally relevant concentrations (<1 ng/mL or ppb) can also be implemented even with a miniaturized device.

From the foregoing, one of ordinary skill in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

---

The invention claimed is:

1. A portable analyzer for detecting bisphenol A, comprising:
 (a) a reaction unit, which comprises:
  (i) a first complex comprising a magnetic bead, a first labeling material, a second labeling material, and an aptamer specifically binding to bisphenol A;
  (ii) a reaction vessel having an inlet, wherein the first complex reacts with bisphenol A to form a second complex comprising the magnetic bead, the first labeling material, and the aptamer and the second labeling material is separated from the first complex; and
  (iii) a means for collecting the second complex in the reaction vessel having a magnetic force source for applying a magnetic force to the reaction vessel in an ON/OFF manner in order to collect the second complex; and
 (b) a detection unit having a means for detecting signals generated from the first and second labeling materials having a photodiode, a charge integrator, or a charge amplifier; and
  wherein the aptamer consists of the nucleotide sequence of SEQ ID NO: 1.

2. The analyzer according to claim 1, wherein the reaction vessel comprises the first complex.

3. The analyzer according to claim 1, wherein the reaction unit further comprises (iv) a means for removing the first complex and bisphenol A, which did not form a second complex, and the separated second labeling material,
 wherein the means for removing further comprises:
  a washing solution vessel comprising a washing solution; and
  a means for transporting the washing solution from the washing solution vessel to the reaction vessel to remove the first complex and bisphenol A, which did not form the second complex, and the separated second labeling material with the washing solution,
  wherein the means for transporting the washing solution has a miniature peristaltic pumps.

4. The analyzer according to claim 3, wherein the reaction unit further comprises (v) a vibrating element for vibrating the reaction vessel and preventing settling of the second complex.

5. The analyzer according to claim 1, wherein the detection unit further comprises a signal-generating means for generating signals from the first labeling material and the second labeling material, respectively,
 wherein the signal-generating means comprises a light-emitting diode (LED), a laser diode (LD), a vertical-cavity surface-emitting laser, a semiconductor diode, or a mercury lamp.

6. The analyzer according to claim 1, wherein each of the first labeling material and the second labeling material is a quantum dot, a fluorescent dye, a radiolabel, or an electrochemical functional group.

7. The analyzer according to claim 1, which further comprises a heat sink or a fan.

8. The analyzer according to claim 5, which further comprises a microcontroller board controlling the means for collecting the second complex, the signal-generating means, and the detection unit in an ON/OFF manner.

9. A method for detecting bisphenol A using the analyzer of claim 1, comprising injecting a collected sample into the inlet of the reaction vessel.

10. The method according to claim 9, wherein the injection of the sample into the inlet is performed by simultaneously or sequentially injecting a collected sample, and a first complex comprising a magnetic bead, a first labeling material, a second labeling material, and the aptamer.

11. A method for detecting bisphenol A using the analyzer of claim 2, comprising injecting a collected sample into the inlet of the reaction vessel.

12. A method for detecting bisphenol A using the analyzer of claim 3, comprising injecting a collected sample into the inlet of the reaction vessel.

* * * * *